US006541026B2

(12) United States Patent
Siskind

(10) Patent No.: US 6,541,026 B2
(45) Date of Patent: Apr. 1, 2003

(54) NUTRITIONAL COMPOSITION, METHODS OF PRODUCING SAID COMPOSITION AND METHODS OF USING SAID COMPOSITION

(76) Inventor: Harry J. Siskind, 202 Bluffhollow, San Antonio, TX (US) 78216

( * ) Notice: Subject to any disclaimer, the term of this patent is extended or adjusted under 35 U.S.C. 154(b) by 90 days.

(21) Appl. No.: 09/740,171

(22) Filed: Dec. 18, 2000

(65) Prior Publication Data

US 2001/0048952 A1 Dec. 6, 2001

Related U.S. Application Data

(60) Provisional application No. 60/171,267, filed on Dec. 16, 1999.

(51) Int. Cl.$^7$ .............................................. A61K 47/00

(52) U.S. Cl. ...................... 424/439; 424/400; 424/441; 424/484; 424/488; 424/725

(58) Field of Search ................................ 424/646, 655, 424/681, 682, 400, 439, 484, 488, 725

(56) References Cited

U.S. PATENT DOCUMENTS

| | | | | |
|---|---|---|---|---|
| 4,216,234 | A | | 8/1980 | Rawlings et al. ............... 426/2 |
| 5,389,395 | A | | 2/1995 | Joseph et al. .................. 426/72 |
| 5,567,424 | A | | 10/1996 | Hastings ................... 424/195.1 |
| 5,612,039 | A | | 3/1997 | Policappelli ............. 424/195.1 |
| 5,626,849 | A | | 5/1997 | Hastings et al. .......... 424/195.1 |
| 5,976,568 | A | | 11/1999 | Riley .......................... 424/451 |
| 5,976,580 | A | | 11/1999 | Ivey et al. ....................... 426/2 |
| 5,985,339 | A | | 11/1999 | Kamarei ...................... 426/72 |
| 6,019,976 | A | * | 2/2000 | Bryant ..................... 424/195.1 |
| 6,168,802 | B1 | | 1/2001 | Howard et al. .............. 424/439 |
| 6,224,871 | B1 | * | 5/2001 | Hastings et al. .......... 424/195.1 |
| 6,245,360 | B1 | | 6/2001 | Markowitz ................... 424/641 |
| 6,270,774 | B1 | | 8/2001 | Hsia et al. ................ 424/195.1 |
| 6,277,842 | B1 | | 8/2001 | Carthron ..................... 514/188 |
| 6,291,533 | B1 | | 9/2001 | Fleischner .................. 514/682 |

OTHER PUBLICATIONS

Article entitled, "Effects of Liquid Proloads with Different Frucloso/Fibre Concentrations on Subsequent Food Intake and Ratings of Hunger in Woman", by M.L.H.M. Van de Ven, et al, Appetite, pp. 130–146 (1984), published in the Netherlands.

Article entitled, "Influence of dietary spices or their active principles on digestive small Intestinal mucosa in rats", by Platel et al., International Journal of Food Sciences and Nutrition, pp. 47, 55–58 (1996), published in Mysore India.

Article entitled, "Effect of Guar Gum on Body Weight and Serum Lipids in Hypercholesterolemic Females", by Tuomilehto et al, Acta Med Scand, pp. 46–48, (1980), published in Kuoplo, Finland.

Article entitled, "Effect of guar gum on body–weight, hunger ratings and metabolism in obese subjects", by M. Krotklewski, British Journal of Nutrition pp. 62, 97–105, (1984).

Article entitled, "Guar Gum for Body Weight Reduction: Meta–analysis of Randomized Tralls", by Pittler, MD et. al.; Excerpta Medica Inc. (2001).

Article entitled, "Bulking Agents in the Treatment of Obesity", by Evans et al.; Nutr. Motabol. 199–203 (1975).

Article entitled, "Effect of guar gum on hunger and satiety after meals of differing fact content: relationship with gastric emptying 1,2," by J. French et al., American Society for Clinical Nutrition, pp. 87–91 (1994).

Article entitled, "Oat gum lowers glucose and insulin after an oral glucose load 1–4", by J. Braaten et al.; American Society for Clinical Nutrition, pp. 1425–30, (1991).

Article entitled, "Guar gum Improves insulin sensitivity, blood lipids, blood pressure, and fibrinolysis in healthy men 1–3", by K. Landin et al., American Society for Clinical Nutrition, pp. 1081–5, (1992).

Article entitled, "Does adding fibre to a low energy, high carbohydrato, low fat diet confer and benefit to the management of newly diagnosed overweight type II diabetics", by V. A. Beattie et al., British Medical Journal, vol. 298 (Apr. 1988).

Article entitled, "Dietary fiber and blood lipids; reduction of serum chloresterol in type II hyperlipidomia by guar gum 1,2", by D. JA Jenkins et al.; The American Journal of Clinical Nutrition; pp. 16–18 (January 1979).

Article entitled, "Metabolizable Energy of Diets Low or High in Dietary Fiber from Cereals when Eaten by Humans 1", by E. Wisker et al.; American Institute of Nutrition, pp. 945–952; (1985).

Article entitled, "Nitrogen Retention, Muscle Creatine and Orotic Acid Excretion in Traumatized Rats Fed Arginine and Glycine Enriched Diets [1]", M. Minuskin et al., published Dec. 1980.

Article entitled, "Acute Effect of Amino Acid Ingestion and Resistance Exercise on Plasma Growth Hormone Concentration in Young Men", by R. Suminski et al., International Journal of Sport Nutrition, pp. 48–00, (1997).

Article entitled, "Effects of arginine and ornithine on strength, lean body mass and urinary hydroxyproilne in adult males", by R. Elam et al., The Journal of Sports Medicine and Physical Fitness, (Mar. 1989).

(List continued on next page.)

*Primary Examiner*—Thurman K. Page
*Assistant Examiner*—Charesse L. Evans
(74) *Attorney, Agent, or Firm*—Kenyon & Kenyon

(57) ABSTRACT

Nutritional compositions comprising aloe vera, hydrolyzed collagen, garcinia cambogia, chromium polynicotinate, chromium picolinate, chromium cruciferate, conjugated linoleic acid, fiber and natural amino acids are disclosed. Nutritional compositions comprising aloe vera, hydrolyzed collagen, garcinia cambogia tea, fenugreek tea, coleus forskohli tea, chromium polynicotinate, chromium picolinate, chromium cruciferate, conjugated linoleic acid, fiber and natural amino acids are also disclosed. Methods for preparing and using these compositions are additionally provided.

57 Claims, No Drawings

OTHER PUBLICATIONS

Article entitled, "Morphological Changes in Adult Males from Resistance Exercise and Amino Acid Supplementation", by R. Elam, The Journal of Sports Medicine and Physical Fitness, (Mar. 1988).

Article entitled, "Low–Dose Amino Acid Supplementation: No Effects on Serum Human Growth Hormone and Insulin In Male Weightlifters", by G. Fogelholm et al., International Journal of Sport Nutrition, pp. 290–297, (1993).

Article entitled, "Phosphollpid breakdown and choline release under hypoxic conditions: Inhibition by biloballdo, a constituent of Ginkgo biloba", by J. Klein et al., Elsevier Science B.V., (1997).

Article entitled, "L–Carnitine Supplementation in Humans. The Effects on Physical Performance", by P. Cerretelli et al., Int. J. Sports Med., pp. 1–14; (1990).

Article entitled, "Effects of L–carnitine supplementation on physical performance and energy metabolism of endurance–trained athletes: a double–blind crossover field study", by P. Colombani et al. Eur J. Appl Physiol; pp. 434–439, (1996).

Article entitled, "Herbal Drugs and Phytopharmaceuticals", by F.C. Czygan et al., Medpharm (1985).

Article entitled, "Aloe vera: a systematic review of its clinical effectiveness", by B. Vogler et al., British Journal of General Practice, pp. 823–828, (1999).

Article entitled, "Effect of Aloe Vera Leaves on Blood Glucose Level in Type I and Type II Diabetic Rat Models", by A. Okyar et al., Phytotherapy Research, pp. 157–161, (2001).

Article entitled, "A study of growth hormone release in man after oral administration of amino acids", by A. Isidori et al., Current Medical Research and Opinion, vol. 7, No. 7 (1981).

Article entitled, "Effect of Dietary Lysine Level and Protein Restriction on the Lipids and Carnitine Levels in the Liver of Pregnant Rats", by M.F. Ortega, Ann Nutr Metab, pp. 162–169, (1989).

Article entitled, Utilization of Dietary Precursors for Carnitine Synthesis in Human Adults[1], By C. J. Rebouche et al., American Institute of Nutrition, (1989).

Article entitled, "Chromium picolinate effects on body composition and muscular performance in wrestlers", by L. S. Walker et al., Medicine & Science in Sports & Exercise, (1998).

Article entitled, "Trace Elements in Man and Animals 10", by A. M. Roussel et al.

Article entitled, "Protein degradation in human skeleton muscle tissue: the effect of insulin, leucino, amino acids and Ions", by K. Lundholm et al., Clinical Science, pp. 310–326, (1981).

Article entitled, "Conjugated Linoleic Acid: A Review," by G. Kelly; Abstract.

Article entitled, "Changes in Body Composition with Conjugated Linoleic Acid," by J. Delaney, PhD et al.; Journal of the American College of Nutrition, vol. 18, No. 4; pp. 487S–493S; (2000).

Article entitled, "Conjugated Linoleic Acid Supplementation in Humans; Effects on Body Composition and Energy Expenditure", by. K. L. Zambell et al., Lipds, vol. 35, No. 7 (2000).

Article entitled, "Effect of sucrose and sweeteners on appetite and energy intake", by J.E. Blundell et al.; International Journal of Obesity; pp. S12–S17; (1998).

Article entitled, "Uncoupling Sweetness and Calories: Methodological Aspects of Laboratory Studies on Appetite Control", by J.E. Blundell et al.; Academic Press Limited, (1988).

Article entitled, "Aspartame Ingested Without Tasting Inhibits Hunger and Food Intake" by P.J. Rogers et al., Physiology & Behavior, vol. 47, pp. 1239–1243, (1990).

Article entitled, "Safety and efficacy of treatment with an ephedrine/caffeine mixture. The first double–blind placebo–controlled pilot study in adolescents", D. Molnar et al., International Journal of Obesity, pp. 1573–1578; (2000).

Article entitled, "An Evaluation of the Effect of Aspartame on Weight Loss", by B. Kanders et al., Appetite, pp. 73–84, (1988).

Article entitled, Effect ofStevie Rebaudiana on Glucose Tolerance In Norman Adult Humans, by R. Curi et al., Brazilian J. Mod Biol Res; pp. 771–774, (1988).

Article entitled, "Recommended Dietary Allowances", 10th Edition, National Academy Press, (1998), published Washington, D.C.

Article entitled, "Carnitine In Muscle, Serum, and Urine of Nonprofessional Athletes: Effects of Physical Exercise, Training, and L–Carnitine Administration", J. Arenas et al.; Muscle & Nerve, pp. 508–604; (1991).

Article entitled, "Chromium (III) picolinate produces chromosome damage in Chines hamster ovary cells", by D. M. Stearns et al., The FASEB Journal, vol. 8, (1995).

Article entitled, "Conjugated Linoleic Acid Supplementation in Humans; Effects on Fatty Acid and Glycerol Kinetics", by K. Zambell et al., Lipids, vol. 36, No. 8, (2001).

Article entitled, Conjugated Linoleic Acid Reduces Body Fat Mass In Overweight and Obese Humans[1], by H. Blankson et al., American Society for Nutritional Sciences, (2000).

Article entitled, "Conjugated linoleic acid (CLA) reduces abdominal adlpose tissue in obese middle–age men with signs of the metabolic syndrome: a randomized controlled trial", by U. Riserus et al., International Journal of Obesity, pp. 1129–1135, (2001).

Article entitled, "Conjugated Linoleic Acid Supplemantation In Humans –Metabolic Effects", by A. Smedman et al., Lipids, vol. 36, No. 8 (2001).

Article entitled, "Conjugated Linoleic Acid (CLA), Body Fat, and Apoptosis", by J. Miner et al., Obesity Research, vol. 9, No. 2 (Feb. 2001).

Article entitled, "Antioxidants, Carnitine, and Chioline as Putative Ergogenic Acids", by M. Kanter et al., International Journal Nutrition, pp. S120–S131, (1996).

Article entitled, "Carnitine and Physical Exercise", by O. J. Heinonen, Sports Medicin (1988).

Article entitled, "Carnitine Metabolism During Exercise", by E. Brass et al., Life Sciences, vol. 54, No. 19, pp. 1383–1393, (1994).

Article entitled, "Dietary–dependent carnitine deficiency as a cause of nonketolic hypoglycemia in an infant", by A. E. Slonim et al., The Journal of Pediatrics, (1981).

Article entitled, "Enhanced lipid utilization in Infants receiving oral–L–carnitine during long–term parentoral nutrition", by R.A. Helms et al., The Journal of Pediatrics (Dec. 1988).

Article entitled, "Arginine Potentiatos the GHRH–But Not The Pyridostigmine–Induced GH Secretion in Normal Short Children. Further Evidence for a Somatostatin Suppressing Effect of Arginine", E. Ghigo et al., Clinical Endocrinology, pp. 763–767, (1990).

Article entitled, "Differential effects of arginine on growth hormone releasing hormone and insulin induced growth hormone secretion", by H.P. Koppeschaar et al., Clinical Endocrinology, pp. 487–490, (1992).

Article entitled, "Insulin–induced hypoglycemia, L–dopa and arginine stimulate GH secretion through different mechanisms in man", by A. Masuda et al., Regulatory Peptides, pp. 53–64, (1990).

Article entitled, "The Effect of a Carbohydrate–Arginine Supplement on Postexercise Carbohydrate Metabolism", B. Yaspelkis et al., International Journal of Sport Nutrition, pp. 241–250, (1999).

Article entitled, "Glycine stimulates growth hormone release in man", by K. Kasai, ACTA Endocrinologica, pp. 283–286, (1980).

Article entitled, "Stimulatory Effect of Glycine on Human Growth Hormone Secretion", by K. Kasai et al., Metabolism, vol. 27, No. 2, (Feb. 1978).

Article entitled, "Low Plasma Carnitine in Patients on Prolonged Total Parental Nutrition: Association with Low Plasma Lysine", by Y. Berner et al., Journal of Parenteral and Enteral Nutrition, vol. 14, No. 3, (1998).

Article entitled, "Lysine Deficiency and Carnitine in Male and Female Rats[1]," by P. Borum et al. Published Nov. 1976.

Article entitled, "Tissue Carnitine Deficiency due to Dietary Lysine Deficiency: Triglycorido Accumulation and Concomitant Impairment in Fatty Acid Oxidation", by L. Khan et al., published Mar. 1976.

Article entitled, "Failure of Commercial Oral Amino Acid Supplements to Increase Serum Growth Hormone Concentrations in Male Body–Builders", by M. Lambert, et al., International Journal of Sport Nutrition, pp. 298–305, (1993).

Article entitled, "Omithine Ingestion and Growth Hormone Release in Bodybuilders", by L. Bucci et al., Nutrition Research, vol. 10, pp. 239–245 (1990).

Article entitled, "Carnitine Biosynthesis from Ψ–Butyrobeteine and from Exogonous protein–bound 6–N–Trimethyl–L–lysine by the Perfused Guinea Pig", The Journal of Biological Chemistry, pp. 1076–10770, (1984).

Article entitled, "Effect of Asorbic Acid Deficiency on the In Vivo Synthesis of Carnitine", by P. Nelson et al., Biochimea et Biophysics Acts, (1981).

Article entitled, "The Antidiabetic Activity of Aloes: Preliminary Clinical and Experimental Observations", by N. Ghannam et al., pp. 288–294, (1988).

Article entitled, "The Effect of a Plants Mixture Extract on Liver Gluconoogenesis In Streptozotocin Induced Diabetic Rats", by F. Al–Awadi et al., Diabetes Research, pp. 183–188, (1991).

Article entitled, "Effects of Low Molecular Constituents From Aloe Vera Gel on Oxidative Metabolism and Cytotoxic and Bacterial Activities of Human Neutrophis", by L.A. Hart et al., Int. J. Immunopharmac, vol. 12, No. 4, pp. 427–434, (1990).

Article entitled, "Effect of Central Chollnorgic Neurotransmission Enhancement by Pyridostigmino on the Growth Hormone Secretion Elicited by Clonidino, Arginine, or Hypoglycemia in Normal and Obese Subjects", by F. Cordido et al., Journal of Clinical Endocrinology and Metabolism, (1990).

Article entitled, "Hyperglycemia and Arginine–Initiated Growth–Hormone Release During Pregnancy", by J.E. Tyson, et al., (Sep. 1989).

Article entitled, "Effect of Arginine on Serum–Levels of Human Growth–Hormone", Floyd et al., Preliminary Communications, (Oct. 1905).

Article entitled, "Stimulation of Insulin Secretion by Amino Acids", by Floyd et al., Journal of Clinical Investigation, vol. 45, No. 9, (1990).

Article entitled, "Interaction of Free Fatty Acids and Arginine on Growth Hormone Secretion in Man", by Maccario et al., Metabolism, vol. 43, No. 2, pp. 223–228, (Feb. 1994).

Article entitled, "Effects of Ornithine or Arginine Administration on Serum Amino Acid Levels", by K. Iwasaki et al, Biochemistry International, vol. 14, No. 6, pp. 971–976, (May 1987).

Article entitled, "The effectiveness of long–term fibre supplementation on weight maintenance in weight–reduced women", by W.J. Pasman et al., International Journal of Obesity; pp. 548–556, (1997).

Article entitled, "Effects of a Cereal Rich In Soluble Fiber on Body Composition and Dietary Compliance during Consumption of a Hypocaloric Diet", by E. Satzman, MD et al., Journal of the American College of Nutrition; pp. 50–67 (2001).

Article entitled, "Effect of psyllium gum and wheat bran on spontaneous energy intake 1–3", by J. Stevens, PhD et al., American Society for Clinical Nutrition; pp. 812–7 (1987).

Article entitled, "Spontaneous weight loss during 11 weeks' ad *libitum* intake of a low fat/high fiber diet in young, normal weight subjects", by A. Raben et al., International Journal of Obesity; pp. 916–923; (1996).

Article entitled, "Dietary Composition, Body Weight, and NIDDM", by K.Z. Walker, PhD et. al, Diabetic Care,; vol. 18, #3 (Mar. 1995).

Article entitled, "Effect of One Week of Fibre Supplementation on Hunger and Safety Ratings and Energy Intake", by W.J. Pasman et al., Appetito, pp. 77–87 (1997).

Article entitled, "Chromium and Diabetes", Nutrition, vol. 15, No. 9, (1988).

Article entitled, "Chromium, Glucose Intolarance and Diabetes", by R.A. Anderson, PhD, FACN; Journal of the American College of Nutrition, vol. 17, No. 6, 548–555; (1998).

Article entitled, "Characteristics of Acidic, Basic and Neutral Amino Acid Transport In the Parfused Rat Hindlimb", by H.S. Hundal et al.; Journal of Physiology, pp. 83–144 (1989).

Article entitled, Lilly Lecture 1979, "Role of Insulin in the Regulation of Protein Synthesis", by Leonard S. Jefferson, Diabetes, vol. 29, (Jun. 1980).

Article entitled, "Cellular Mechanisms Involved in the Action on Insulin on Protein Synthesis", by S.R. Kimball et al., Diabetes/Metabolism Reviews, vol. 4, No. 8,; pp. 773–787; (1988).

Article entitled, "Physiologic Hyperinsulinemia Stimulates Protein Systhesis and Enhances Transport of Selected Amino Acids in Human Skeletal Muscle", by G. Biolo et al.; The American Society for Clinical Investigation, Inc. vol. 95, pp. 811–819 (Feb. 1995).

Article entitled, "The Effect of Systemic Hyperinsulinemia With Concomitant Amino Acid Infusion on Skeletal Muscle Protein Turnover in the Human Forearm", by E. Newman et al.; Metabolism, vol. 43, No. 1; pp. 70–78 (Jan. 1994).

Article entitled, Dietary carnitine intake related to skeletal muscle and plasma carnitine concentrations in adult men and women[1-3], by D.F. Lennon et al., The American Journal of Clinical Nutrition, pp. 234–238, (Feb. 1986).

Article entitled, "Effect of L–Carnitine Supplementation on Muscle and Blood Carnitine Content and Lactate Accumulation During High–Intensity Sprint Cycling", by C. Barnett et al., International Journal of Sport Nutrition, pp. 280–288, (1994).

Article entitled, "Carnitine supplementation: effect of muscle carnitine and glycogen content during exercise", by M. Vukovich et al., Medicine and Science in Sports and Exercise, (Mar. 1994).

Article entitled, "Morphometric Evidence of the Trophic Effect of L–Carnitine on Human Skeletal Muscle", by L.G. Spagnoli et al., pp; 18–23, (1990).

Article entitled, "Effect of Aspastame Asparegino, and Carnitine Supplementation in the Diet on Metabolism of Skeletal Muscle During a Moderate Exercise", by A. Lancha, Jr., et al., Physiology & Behavior, vol. 57, No. 2, pp. 367–371 (1995).

Article entitled, "L–Carnitine Supplementation in Humans, The Effects on Physical Performance", by P. Cerretelli et al., Int. J. Sports Med. II ; pp. 1–14, (1980).

Article entitled, "Metabolic changes induced by maximal exercise in human subjects following L–Carnitine administration", by N. Siliprandi et al., Biochimica et Biophysica Acta. ; pp. 17–21 (1990).

Article entitled, "Prolonged submaximal exercise and L–carnitine in humans", by S. Oyono–Enguelle, et al.; European Journal of Applied Physiology, pp. 53–81, (1988).

Article entitled, "Respiratory Chain Enzymes in Muscle of Endurance Athletes: Effect of L–Carnitine", by R. Huertas et al., Biochemical and Biophysical Research Communications, vol. 188, No. 1, (1992).

Article entitled, "L–Carnitine Improves Glucose Disposal in Type 2 Diabetic Patients", by G. Mingrone et al., Journal of the American College of Nutrition, vol. 18, No. 1, pp. 77–82, (1999).

Article entitled, Effect of Dietary macronutrient content on carnitine excretion and efficiency of carnitine reabsorption[1-3], by D. D. Stadler et al., American Society for Clinical Nutrition, pp. 866–872 (1993).

Article entitled "Chromium and exercise training; effect on obese women", by Grant et al., Medicine & Science in Sports & Exercise, May 1997.

Article entitled "Effects of Chromium Picolinate Supplementation on Body Composition: A Radonmized, Double–Masked, Placebo–Controlled Study", by Kaats et al., Current Therapeutic Research, vol. 57, No. 10, Oct. 1996.

Article entitled, "Effects of Niacin–bound chromiun supplementation on body composition in overweight African–American women", by V. Crawford, et al.; Diabetes, Obesity and Metabolism, pp. 331–337, 1989.

Article entitled, "Composition and Biological Activity of Chromium–Pyridine Carboxylate Complexes", by G.W. Evand et al., Journal of Inorganic Biochemistry, pp. 177–187, 1993.

Article entitled, "Effects of Chromium Picolinate Supplementation on Body Composition, Strength, and Urinary Chromium Loss in Football Players", by Clancy et al.; International Journal of Sport Nutrition, pp. 142–153; 1994.

Article entitled, "Effect of Chromium Supplementation and Exercise on Body Composition, Resting Metabolic Rate and Selected Biochemical Parameters in Moderately Obese Women Following an Exercise Program", Volpe et al., Journal of the American College of Nutrition, vol. 20, No. 4, pp. 293–306; 2001.

Article entitled, "Effects of Chromium picolinate on body composition", by Trent et al.; The Journal of Sports Medicine and Physical Fitness, vol. 35 –No. 4; 1995.

Article entitled, "Effects of resistance training and chromium picolinate on body composition and skeletal muscle in older men", By W. Campbell, et al., American Physiological Society, pp. 29–39; 1999.

Article entitled, "Effects of chromium and resistive training on muscle strength and body composition", by M. Hallmark et al., Medicine and Science in Sports and Exercise; pp. 130–143; 1996.

Article entitled, Chromium supplementation and resistance training: effects on body composition, strength, and trace element status us men [2-4].

Article entitled, "The effectiveness of long–term supplementation of carbohydrate, chromium, fibro and caffeine on weight maintenance", W. J. Pasman, et al., International Journal of Obesity; pp. 1143–1151, (1097).

Entitled, "A Randomized, Double–Masked, Placebo–Controlled Study of the Effects of Chromium Picolinate Supplementation on Body Composition; a Replication and Extension of a Previous Study", by G. R. Kaats et al.; Current Therapeutic Research, vol. 69 No. 6, (1998).

Article entitled, "The Nutritional Supplement Chromium (III) Tris(picolinate) Cleaves DNA", by J. K. Speetjens et al., American Chemical Society, pp. 483–487; (1999).

Article entitled, "The effectiveness of popular, non–prescription weight loss supplements", by G. Egger et al., MJA, vol. 171, pp. 604–608, 1999.

Article, "The Effect of an Herbal Dietary Supplement Containing Ephedrine and Caffeine on Oxygen Consuption in Humans", by F. L. Greeway et al.; The Journal of Alternative and Complementary Medicine, vol. 6; pp. 553–555, (2000).

* cited by examiner

NUTRITIONAL COMPOSITION, METHODS OF PRODUCING SAID COMPOSITION AND METHODS OF USING SAID COMPOSITION

This application claims the benefit of U.S. Provisional Application No. 60/171267, filed Dec. 16, 1999.

FIELD OF THE INVENTION

The present invention provides nutritional compositions comprising aloe vera, hydrolyzed collagen, garcinia cambogia, chromium polynicotinate, chromium picolinate, chromium cruciferate, conjugated linoleic acid, fiber and natural amino acids. The instant invention also provides nutritional compositions comprising aloe vera, hydrolyzed collagen, garcinia cambogia tea, fenugreek tea, coleus forskohli tea, chromium polynicotinate, chromium picolinate, chromium cruciferate, conjugated linoleic acid, fiber and natural amino acids. The invention additionally contemplates methods for preparing these compositions and methods of using the compositions.

BACKGROUND OF THE INVENTION

It has now been discovered that a nutritional composition comprising aloe vera, hydrolyzed collagen, garcinia cambogia tea, fenugreek tea, coleus forskohli tea, chromium polynicotinate, chromium picolinate, chromium cruciferate, conjugated linoleic acid, fiber and natural amino acids effectively assists in the reduction of body fat, enhancement of nutrient absorption, and formation and protection of lean muscle tissue. The composition may also possess antioxidant properties.

OBJECTS AND SUMMARY OF THE INVENTION

The present invention provides a nutritional composition comprising aloe vera, collagen, preferably hydrolyzed collagen, garcinia cambogia, chromium polynicotinate (commercially available as ChromeMate®), chromium picolinate, chromium cruciferate, conjugated linoleic acid, fiber and natural amino acids. The instant invention also provides a nutritional composition comprising aloe vera, collagen, preferably hydrolyzed collagen, garcinia cambogia tea, fenugreek tea, coleus forskohli tea, chromium polynicotinate, chromium picolinate, chromium cruciferate, conjugated linoleic acid, fiber and natural amino acids. The composition of the instant invention helps reduce body fat in humans and enhances the human body's use and absorption of nutrients. The composition of the present invention is also useful in promoting the formation and protection of lean muscle tissue in humans. The composition of the present invention may also possess antioxidant properties. The composition may possess additional beneficial properties. The composition of the instant invention can be provided in a variety of forms. Thus, beverages, foods, dietary supplements, and nutraceutical products containing the nutritional composition of the instant invention are included in the scope of the invention.

The present invention further provides a process for producing the compositions of the invention. This process includes, but is not limited to, certain heating, homogenization, and cooling steps.

The present invention additionally provides a process for maintaining the components of the composition in solution. Such process includes, but is not limited to, the addition of glycerin and/or natural ingredients to the composition.

DETAILED DESCRIPTION OF THE INVENTION

The present invention provides a nutritional composition comprising aloe vera, hydrolyzed collagen, garcinia cambogia, chromium polynicotinate, chromium picolinate, chromium cruciferate, conjugated linoleic acid, fiber and natural amino acids. The instantly claimed invention further provides a nutritional composition comprising aloe vera, hydrolyzed collagen, garcinia cambogia tea, fenugreek tea, coleus forskohli tea, chromium polynicotinate, chromium picolinate, chromium cruciferate, conjugated linoleic acid, fiber and natural amino acids. The composition can exist in many forms, including dry, powder or aqueous forms. The aloe vera of the present invention can exist in many forms, including concentrated, dry or aqueous forms. Aloe vera contains over 200 nutrients that benefit the immune system and digestive tract. Where the composition of the instant invention is in dry form, aloe vera is present in the composition in concentrated, dry form in an amount of about 0.06–0.25% by weight, preferably about 0.065%–0.2%, more preferably about 0.07%–0.15%, yet more preferably about 0.075–0.1%, still more preferably about 0.075%. Where the composition is in a liquid or aqueous form, concentrated, dry aloe vera is reconstituted with water to arrive at a final 200:1 ratio. Where the composition is in a liquid or aqueous form, aloe vera is present in the composition in an amount of up to about 50% by weight, preferably about 13–40%, more preferably about 14–30%, yet more preferably about 15–20%, still more preferably about 15%.

Collagen is a protein which can be found in skin, bones, and lean muscle tissue. Collagen assists the body in building lean muscle tissue. Preferably, the collagen utilized in the nutritional composition of the instant invention is in a hydrolyzed form. The collagen, preferably in hydrolyzed form, of the nutritional composition of the instant invention is present in an amount of up to about 30% by weight, preferably about 11%–25%, more preferably about 11.5%–20%, yet more preferably about 12%–15%, still more preferably about 12.5%.

The garcinia cambogia, fenugreek and coleus forskohli utilized in the nutritional composition of the instant invention comprise herbal extracts of garcinia cambogia, fenugreek and coleus forskohli, respectively. Since garcinia cambogia as well as fenugreek and coleus forskohli are not readily soluble in water, these components are preferably present as liquid tea extracts. Such teas are prepared by placing garcinia cambogia, fenugreek and/or coleus forskohli in boiling water for a time sufficient to produce a concentrated tea extract. Where the instantly claimed compositions are in liquid or aqueous form, garcinia cambogia tea, fenugreek tea and coleus forskohli tea are each present in an amount of about 0.005–5% by weight, preferably about 0.5%.

The chromium component of the instantly claimed nutritional composition comprises chromium picolinate, chromium polynicotinate, chromium cruciferate, or mixtures thereof. The term "chromium mixture" as used herein refers to a mixture of chromium picolinate, chromium polynicotinate and chromium cruciferate. The chromium utilized in the composition of the present invention preferably comprises a chromium mixture. The chromium mixture is present in an amount of about 0.00005%–0.0003 by weight, preferably about 0.0001%. The chromium polynicotinate utilized in the composition of the present invention is commercially available as ChromeMate®.

The conjugated linoleic acid of the nutritional composition of the instant invention is present in an amount of about 0.000005%–0.0003% by weight, preferably about 0.00001%.

The natural amino acids of the instant invention comprise L-lysine, preferably in an amount of about 0.005–5% by weight, preferably about 0.2393%, more preferably about 0.1000%; L-ornithine, preferably in an amount of about 0.005–5% by weight, preferably about 0.2019%, more preferably about 0.0750%; L-arginine, preferably in an amount of about 0.005–5% by weight, preferably about 0.2019%, more preferably about 0.0750%; L-carnitine, preferably in an amount of about 0.005–5% by weight, preferably about 0.2393%, more preferably about 0.0750%; trimethylglycine, preferably in an amount of about 0.005–5% by weight, preferably about 0.1835%, more preferably about 0.0750%; and L-glycine, preferably in an amount of about 0.005–5%, preferably about 0.1500%.

The fiber of the nutritional composition of the instant invention is present in an amount of about 0.8–18% by weight, preferably about 7.409% by weight. Preferably, natural chicory extract, which is a soluble dietary fiber, is utilized.

The nutritional composition of the instant invention is useful for reducing human body fat, promoting the formation and protection of human lean muscle tissue, and enhancing the human body's use and absorption of nutrients. Reduction of body fat can be measured by methods known in the art, including measuring weight loss. Formation and protection of human lean muscle tissue as well as enhancement of use and absorption of nutrients can be evaluated and measured by appropriate methods known in the art. The composition of the present invention is also useful as an antioxidant. The composition may also possess additional beneficial properties including aiding in the healing and/or repair of human body tissue, treatment of various human ailments and/or prevention or amelioration of the ill effects of aging on the human body. The nutritional composition can be provided in a variety of forms. Accordingly, beverages, foods, dietary supplements, and nutraceutical products containing the nutritional composition of the instant invention may be produced. Preferably, the nutritional composition of the instant invention is utilized in dietary supplement beverages. Where the nutritional composition of the instant invention is employed in a dietary supplement beverage, additional ingredients such as the herbal extract stevia can be added as well as natural flavors such as strawberry and kiwi. Additionally, preservatives such as sodium benzoate may be added to increase the longevity of the dietary supplement beverage.

Where the nutritional composition of the present invention is utilized in a dietary supplement beverage, one tablespoon of such beverage along with a glass of water is preferably ingested at nighttime prior to sleeping. While the composition can be consumed anytime, it is preferred to be consumed about 2–3 hours after last eating, and preferably about 3 hours after eating. Moreover, ingesting the nutritional composition of the instant invention immediately prior to sleeping allows for optimal healing and repair of the body. Preferably, no food or drinks, except for water, should be ingested for a minimum of three hours prior to ingesting the beverage. Preferably, the dietary supplement beverage should be consumed every day. The dietary supplement beverage can also be ingested more than once a day and at times other than nighttime.

The instant invention further provides methods for maintaining the components of the nutritional composition of the present invention in solution. Such methods include, but are not limited to the addition of glycerin and/or natural ingredients. Such methods comprise adding to the composition glycerin in an amount of about 2–5% by weight, preferably about 2.5%, and/or natural ingredients in amounts effective to maintain the components of the composition of the instant invention in solution.

A dietary supplement beverage comprising the nutritional composition of the instant invention can be produced by combining glycerin, collagen, preferably hydrolyzed in form, conjugated linoleic acid, xanthan gum, aloe gel powder, L-lysine, L-ornithine, L-arginine, L-carnitine, trimethylglycine, L-glycine, stevia, garcinia cambogia tea, fenugreek tea, coleus forskohli tea, a chromium mixture, citric acid, sodium benzoate, potassium sorbate, soluble dietary fiber, natural kiwi and strawberry flavor, and purified water in amounts in accordance with the invention.

The instant invention additionally relates to processes for producing dietary supplement beverages comprising the nutritional composition of the present invention. Such processes include, but are not limited to heating and homogenization of the collagen and conjugated linoleic acid prior to addition of the collagen and conjugated linoleic acid to the dietary supplement beverage. Such processes comprise, prior to addition of the glycerin and collagen to the dietary supplement beverage, heating the glycerin and collagen to about 70–80° C., preferably about 75° C.; followed by homogenization of the glycerin and collagen for about 20–40 minutes, preferably about 30 minutes; followed by addition of the collagen and glycerin to the nutritional composition of the dietary supplement beverage described herein above. The processes further comprise, prior to addition of the purified water, conjugated linoleic acid, and xanthan gum to the dietary supplement beverage formulation, heating said purified water, conjugated linoleic acid, and xanthan gum to about 60–70° C., preferably about 65° C.; followed by homogenization of the purified water, conjugated linoleic acid, and xanthan gum for about 40–50 minutes, preferably about 45 minutes; followed by addition of the purified water, conjugated linoleic acid, and xanthan gum to the nutritional composition of the dietary supplement beverage described herein above.

What is claimed is:

1. A nutritional composition comprising aloe vera, collagen, garcinia cambogia, chromium polynicotinate, conjugated linoleic acid, fiber and natural amino acids in amounts effective to help reduce body fat in humans.

2. A nutritional composition comprising aloe vera, collagen, garcinia cambogia, chromium polynicotinate, conjugated linoleic acid, fiber and natural amino acids in amounts effective to help enhance nutrient absorption in humans.

3. A nutritional composition comprising aloe vera, collagen, garcinia cambogia, chromium polynicotinate, conjugated linoleic acid, fiber and natural amino acids in amounts effective to help promote the formation and protection of lean muscle tissue in humans.

4. A nutritional composition comprising aloe vera, collagen, garcinia cambogia, chromium polynicotinate, conjugated linoleic acid, fiber and natural amino acids in amounts effective to possess antioxidant properties.

5. A nutritional composition comprising aloe vera, collagen, garcinia cambogia tea, fenugreek tea, coleus forskohli tea, a chromium mixture, conjugated linoleic acid, fiber and natural amino acids.

6. A nutritional composition comprising aloe vera, collagen, garcinia cambogia tea, fenugreek tea, coleus forskohli tea, a chromium mixture, conjugated linoleic acid, fiber and natural amino acids in amounts effective to help enhance nutrient absorption in humans.

7. A nutritional composition comprising aloe vera, collagen, garcinia cambogia tea, fenugreek tea, coleus forskohli tea, a chromium mixture, conjugated linoleic acid, fiber and natural amino acids in amounts effective to help promote the formation and protection of lean muscle tissue in humans.

8. A nutritional composition comprising aloe vera, collagen, garcinia cambogia tea, fenugreek tea, coleus forskohli tea, a chromium mixture, conjugated linoleic acid, fiber and natural acids in amounts effective to possess antioxidant properties.

9. A nutritional composition comprising aloe vera, hydrolyzed collagen, garcinia cambogia tea, fenugreek tea, coleus forskohli tea, a chromium mixture, conjugated linoleic acid, soluble dietary fiber, L-lysine, L-ornithine, L-arginine, L-carnitine, L-glycine and trimethylglycine in amounts effective to help reduce body fat in humans.

10. A nutritional composition comprising aloe vera, hydrolyzed collagen, garcinia cambogia tea, fenugreek tea, coleus forskohli tea, a chromium mixture, conjugated linoleic acid, soluble dietary fiber, L-lysine, L-ornithine, L-arginine, L-carnitine, L-glycine and trimethylglycine in amounts effective to enhance nutrient absorption in humans.

11. A nutritional composition comprising aloe vera, hydrolyzed collagen, garcinia cambogia tea, fenugreek tea, coleus forskohli tea, a chromium mixture, conjugated linoleic acid, soluble dietary fiber, L-lysine, L-ornithine, L-arginine, L-carnitine, L-glycine and trimethylglycine in amounts effective to help promote the formation and protection of lean muscle tissue in humans.

12. A nutritional composition comprising aloe vera, hydrolyzed collagen, garcinia cambogia tea, fenugreek tea, coleus forskohli tea, a chromium mixture, conjugated linoleic acid, soluble fiber, L-lysine, L-ornithine, L-arginine, L-carnitine, L-glycine and trimethylglycine in amounts effective to possess antioxidant properties.

13. The nutritional composition of any of claims 1–12 wherein said aloe vera is present in an amount of about 0.06–0.25% by weight where said composition is in dry form, and up to about 50% by weight where said composition is in liquid or aqueous form.

14. The nutritional composition of any of claims 1–12 wherein said aloe vera is present in an amount of about 0.075% by weight where said composition is in dry form, and about 15% by weight where said composition is in liquid or aqueous form.

15. The nutritional composition of any of claims 1–12 wherein said collagen or hydrolyzed collagen is present in an amount of up to about 30% by weight.

16. The nutritional composition of any of claims 1–12 wherein said collagen or hydrolyzed collagen is present in an amount of about 12.5% by weight.

17. The nutritional composition of any of claims 5–12 wherein said garcinia cambogia tea is present in an amount of about 0.005 to 5% by weight.

18. The nutritional composition of any of claims 5–12 wherein said garcinia cambogia tea is present in an amount of about 0.5% by weight.

19. The nutritional composition of any of claims 5–12 wherein said fenugreek tea is present in an amount of about 0.005 to 5% by weight.

20. The nutritional composition of any of claims 5–12 wherein said fenugreek tea is present in an amount of about 0.5% by weight.

21. The nutritional composition of any of claims 5–12 wherein said coleus forskohli tea is present in an amount of about 0.005 to 5% by weight.

22. The nutritional composition of any of claims 5–12 wherein said coleus forskohli tea is present in an amount of about 0.5% by weight.

23. The nutritional composition of any of claims 5–12 wherein said chromium mixture is present in an amount of about 0.00005–0.0003% by weight.

24. The nutritional composition of any of claims 5–12 wherein said chromium mixture is present in an amount of about 0.0001% by weight.

25. The nutritional composition of any of claims 1–12 wherein said conjugated linoleic acid is present in an amount of about 0.000005–0.0003% by weight.

26. The nutritional composition of any of claims 1–12 wherein said conjugated linoleic acid is present in an amount of about 0.00001% by weight.

27. The nutritional composition of any of claims 9–12 wherein said L-lysine is present in an amount of about 0.005–5% by weight.

28. The nutritional composition of any of claims 9–12 wherein said L-lysine is present in an amount of about 0.1000% by weight.

29. The nutritional composition of any of claims 9–12 wherein said L-ornithine is present in an amount of about 0.005–5% by weight.

30. The nutritional composition of any of claims 9–12 wherein said L-ornithine is present in an amount of about 0.0750% by weight.

31. The nutritional composition of any of claims 9–12 wherein said L-arginine is present in an amount of about 0.005–5% by weight.

32. The nutritional composition of any of claims 9–12 wherein said L-arginine is present in an amount of about 0.0750% by weight.

33. The nutritional composition of any of claims 9–12 wherein said L-carnitine is present in an amount of about 0.005–5% by weight.

34. The nutritional composition of any of claims 9–12 wherein said L-carnitine is present in an amount of about 0.0750% by weight.

35. The nutritional composition of any of claims 9–12 wherein said L-glycine is present in an amount of about 0.005–5% by weight.

36. The nutritional composition of any of claims 9–12 wherein said L-glycine is present in an amount of about 0.1500% by weight.

37. The nutritional composition of any of claims 9–12 wherein said trimethylglycine is present in an amount of about 0.005–5% by weight.

38. The nutritional composition of any of claims 9–12 wherein said trimethylglycine is present in an amount of about 0.0750% by weight.

39. The nutritional composition of any of claims 1–12 wherein said fiber is present in an amount of about 0.8–18% by weight.

40. The nutritional composition of any of claims 1–12 wherein said fiber is present in an amount of about 7.409% by weight.

41. A dietary supplement beverage comprising the nutritional composition of any one of claims 1–12.

42. A nutritional composition comprising:
  (a) aloe vera in an amount of about 0.075% by weight where said composition is in dry form, and about 15% by weight where said composition is in liquid form;
  (b) collagen, preferably hydrolyzed, in an amount of about 12.5% by weight;
  (c) garcinia cambogia tea in an amount of about 0.5% by weight;

(d) fenugreek tea in an amount of about 0.5% by weight;

(e) coleus forskohli tea in an amount of about 0.5% by weight;

(f) a chromium mixture in an amount of about 0.0001% by weight;

(g) conjugated linoleic acid is present in an amount of about 0.00001% by weight;

(h) L-lysine in an amount of about 0.1000% by weight;

(i) L-ornithine in an amount of about 0.0750% by weight;

(j) L-arginine in an amount of about 0.0750% by weight;

(k) L-carnitine in an amount of about 0.0750% by weight;

(l) L-glycine in an amount of about 0.1500% by weight;

(m) trimethylglycine in an amount of about 0.0750% by weight; and (n) soluble dietary fiber in an amount of about 7.409% by weight.

43. The nutritional composition of claim 42 further comprising:

(o) glycerin in an amount of about 2.5–5% by weight, preferably about 2.5%.

44. A dietary supplement beverage comprising the nutritional composition of claim 42 or 43.

45. A method for producing a dietary supplement beverage comprising the nutritional composition of claim 43 comprising, as a pre-treatment step:

(a) heating said glycerin and collagen to about 70–80° C., about 75° C., (b) homogenization for about 25–35 minutes, about 30 minutes, and (c) adding said glycerin and collagen to said nutritional composition.

46. The method of claim 45 further comprising, as a pre-treatment step:

(d) heating said purified water, conjugated linoleic acid, and xanthan gum to about 60–70° C., about 65° C.;

(e) homogenization for about 40–50 minutes, about 45 minutes; and (f) adding said water, conjugated linoleic acid, and xanthan gum to said nutritional composition.

47. A method for maintaining or increasing the solubility of the nutritional composition of claims 42 or 43 in solution by adding glycerin and/or natural ingredients.

48. The method of claim 47 wherein said glycerin is present in an amount of about 2% to 5% by weight, about 2.5%.

49. A method for reducing the body fat in humans comprising administering the dietary supplement beverage of claim 44 in an amount effective to reduce body fat.

50. A method for enhancing nutrient absorption in humans comprising administering the dietary supplement beverage of claim 44 in an amount effective to enhance nutrient absorption.

51. A method for promoting the formation and protection of lean muscle tissue in humans comprising administering the dietary supplement beverage of claim 44 in an amount effective to promote the formation and protection of lean muscle tissue.

52. The method of claim 49 where said beverage is administered about three hours after eating.

53. The method of claim 50 where said beverage is administered about three hours after eating.

54. The method of claim 51 where said beverage is administered about three hours after eating.

55. The method of claim 52 where the method is repeated each day for a period effective to reduce body fat.

56. The method of claim 53 where the method is repeated each day for a period effective to enhance nutrient absorption.

57. The method of claim 54 where the method is repeated each day for a period effective to promote the formation and protection of lean muscle tissue.

* * * * *